United States Patent [19]

Nakamura et al.

[11] Patent Number: 4,973,351

[45] Date of Patent: Nov. 27, 1990

[54] OXAZOLINE COMPOUNDS AND HERBICIDES CONTAINING THE SAME

[75] Inventors: Yukihiro Nakamura; Takashi Isono; Yuichi Sugiyama, all of Tokyo, Japan

[73] Assignee: SDS Biotech Kabushiki Kaisha, Japan

[21] Appl. No.: 375,836

[22] Filed: Jul. 5, 1989

[30] Foreign Application Priority Data

Jul. 6, 1988 [JP] Japan .................................. 63-166799

[51] Int. Cl.$^5$ .......................................... C07D 263/42
[52] U.S. Cl. .......................................... 71/88; 548/228
[58] Field of Search ............................ 548/228; 71/88

[56] References Cited

U.S. PATENT DOCUMENTS

| | | | |
|---|---|---|---|
| 4,221,584 | 9/1980 | Ziman | 544/228 |
| 4,810,281 | 3/1989 | Palla | 71/88 |
| 4,854,961 | 8/1989 | Wellinga et al. | 71/88 |

*Primary Examiner*—Donald G. Daus
*Attorney, Agent, or Firm*—Webb, Burden, Ziesenheim & Webb

[57] ABSTRACT

Disclosed herein are 4-phenylamino-3-oxazolin-5-one compounds and herbicides comprising as an essential effective ingredient 4-phenylamino-3-oxazolin-5-one compounds.

9 Claims, No Drawings

OXAZOLINE COMPOUNDS AND HERBICIDES CONTAINING THE SAME

FIELD OF THE INVENTION

The present invention relates to novel 4-phenylamino-3-oxazolin-5-one compounds and to herbicides, in particular for use in paddy fields, comprising as an essential effective ingredient 4-phenylamino-3-oxazolin-5-one compound. The proposed oxazoline compounds are also of potential use as medicines, other agricultural pesticides, various industrial chemicals and intermediates for chemical synthesis.

BACKGROUND OF THE INVENTION 4-phenylamino-3-oxazolin-5-one compounds are not described in chemical literatures and patents.

While various herbicides are known in the art, herbicides for use in a paddy field are required to have the following properties.

(i) The compounds have no phytotoxicity to paddy rice, (ii) said compounds exhibit herbicidal activities to weeds, in particular, water chestnut(*Eleocharis kuroguwai*) and water nutsedge(*Cyperus serotinus*).

(iii) said compounds exhibit herbicidal activities even in the treatment of barnyardgrass of the 3-leaf stage.

OBJECT OF THE INVENTION

The present invention has been accomplished in consideration of the prior art as mentioned above, and an object of the invention is to provide compounds which are useful as herbicides, particularly those for use in paddy fields, and herbicides containing said compounds as active ingredients.

SUMMARY OF THE INVENTION

The novel compounds of the present invention are represented by the following general formula [I].

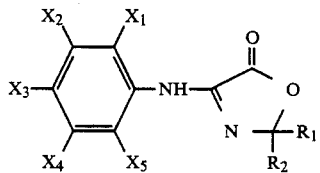

wherein $X_1$, $X_2$, $X_3$, $X_4$ and $X_5$ are each hydrogen, halogen, a lower alkyl, a lower alkoxy, a lower alkylthio, trifluoromethyl, difluoromethoxy, a lower alkoxycarbonyl, nitro or an acyl, and $R_1$ and $R_2$ are each hydrogen, a lower alkyl or phenyl, optionally substituted with halogen atom(s). The herbicides of the present invention comprise as their active ingredient a compound represented by the general formula [I] as mentioned above.

DETAILED DESCRIPTION OF THE INVENTION

The novel compounds and herbicides according to the present invention are illustrated below in detail.

The novel compounds of the invention are represented by the following general formula [I] as mentioned previously.

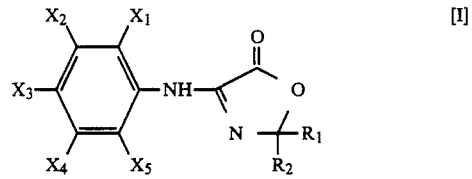

wherein $X_1$, $X_2$, $X_3$, $X_4$ and $X_5$ are each hydrogen, halogen, a lower alkyl, a lower alkoxy, a lower alkylthio, trifluoromethyl, difluoromethoxy, a lower alkoxycarbonyl, nitro and an acyl, and $R_1$ and $R_2$ are each hydrogen, a lower alkyl and phenyl, optionally substituted with halogen atom(s).

In the above formula, the halogen includes chlorine, fluorine and bromine, and the lower alkyl and the lower alkyl moiety in the lower alkoxy, the lower alkylthio and the lower alkoxycarbonyl, include, for example, methyl, ethyl, n-propyl, i-propyl, n-butyl, i-butyl, sec-butyl, t-butyl, n-amyl and i-amyl.

In this connection the compounds represented by the above-mentioned general formula [I] may also exist as tautomers represented by the following general formula [I]'. In the present invention, however, the tautomers represented by the general formula [I]' are encompassed by the compounds represented by the general formula [I].

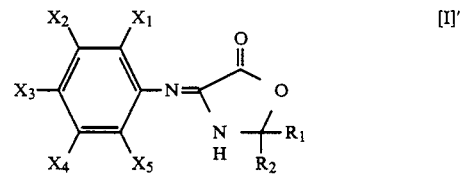

wherein $X_1$, $X_2$, $X_3$, $X_4$ and $X_5$ are as defined above, and $R_1$ and $R_2$ are also as defined above.

The compounds of the general formula [I] according to the invention can be prepared by a process as represented by the following reaction scheme in which $X_1$, $X_2$, $X_3$, $X_4$ and $X_5$, and $R_1$ and $R_2$ have the same meanings as defined above, and R represents a lower alkyl.

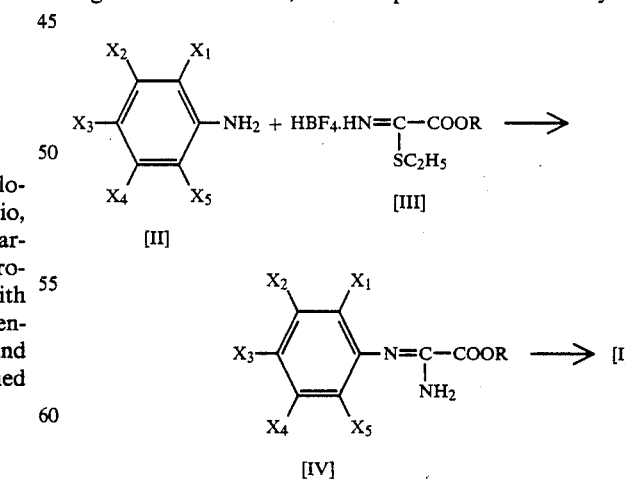

An amine of the general formula [II] is reacted with a compound of the general formula [III], and is then neutralized to provide an ester of the general formula [IV]. The ester [IV] is reacted with a ketone or an aldehyde of the general formula [V], thereby providing the compound [I] according to the invention. The compound [III] can be prepared by reacting a compound of the general formula $H_2NC(S)C(O)OR'$ with a Meerwein reagent (triethyloxonium tetrafluoroborate) in methylene chloride.

Typical examples of the compounds [I] of the present invention are those shown in Table 1. Hereinafter, the compounds of the invention mentioned in the specification will be indicated individually by reference to the compound No. designated in Table 1.

The compounds of the invention are designated by way of the symbols in the aforesaid general formula. In the column showing physical properties of compound shown in Table 1, NMR represents a nuclear magnetic resonance spectrum, the solvent used in the measurement is shown in round brackets, and the unit is ppm. IR represents an infrared spectrum and the unit is $cm^{-1}$.

TABLE 1

| No. | $X_1, X_2, X_3$ $X_4$ and $X_5$ | $R_1$ and $R_2$ | IR (mp °C.) | N.M.R. (CDCl$_3$) |
|---|---|---|---|---|
| 1 | $X_1$ = H<br>$X_2$ = F<br>$X_3$ = H<br>$X_4$ = H<br>$X_5$ = H | $R_1$ = H<br>$R_2$ = H | 3350, 1760<br>1655 | 5.72(s, 2H)<br>6.4–6.9(m)<br>6.9–7.8(m) |
| 2 | $X_1$ = CH$_3$<br>$X_2$ = H<br>$X_3$ = Cl<br>$X_4$ = H<br>$X_5$ = H | $R_1$ = H<br>$R_2$ = H | 3425, 1800<br>1775, 1665 | 2.30(s, 3H)<br>5.70(s, 2H)<br>6.6–7.4(m)<br>7.9–8.3(m) |
| 3 | $X_1$ = H<br>$X_2$ = COCH$_3$<br>$X_3$ = H<br>$X_4$ = H<br>$X_5$ = H | $R_1$ = H<br>$R_2$ = H | 3300, 1780<br>1680, 1650 | 2.58(s, 3H)<br>5.75(s, 2H)<br>7.0–8.4(m) |
| 4 | $X_1$ = H<br>$X_2$ = H<br>$X_3$ = F<br>$X_4$ = H<br>$X_5$ = H | $R_1$ = H<br>$R_2$ = H | 3350, 1775<br>1670 | 5.72(s, 2H)<br>6.7–7.8(m) |
| 5 | $X_1$ = H<br>$X_2$ = Cl<br>$X_3$ = H<br>$X_4$ = H<br>$X_5$ = H | $R_1$ = H<br>$R_2$ = H | 3340, 1775<br>1670 | 5.75(s, 2H)<br>6.8–7.9(m) |
| 6 | $X_1$ = CH$_3$<br>$X_2$ = Cl<br>$X_3$ = H<br>$X_4$ = H<br>$X_5$ = H | $R_1$ = H<br>$R_2$ = H | 3440, 1780<br>1665 | 2.38(s, 3H)<br>5.72(s, 2H)<br>6.8–7.3(m)<br>7.8–8.3(m) |
| 7 | $X_1$ = Cl<br>$X_2$ = Cl<br>$X_3$ = H<br>$X_4$ = H<br>$X_5$ = H | $R_1$ = H<br>$R_2$ = H | 3400, 1785<br>1665 | 5.74(s, 2H)<br>6.9–7.4(m)<br>7.75(m)<br>8.1–8.6(m) |
| 8 | $X_1$ = Cl<br>$X_2$ = Cl<br>$X_3$ = Cl<br>$X_4$ = H<br>$X_5$ = H | $R_1$ = H<br>$R_2$ = H | 3375, 1805<br>1780, 1665 | 5.77(s, 2H)<br>7.0–7.5(m)<br>7.72(m)<br>8.2–8.6(m) |
| 9 | $X_1$ = CH$_3$<br>$X_2$ = H<br>$X_3$ = H<br>$X_4$ = F<br>$X_5$ = H | $R_1$ = H<br>$R_2$ = H | 3375, 1780<br>1650 | 2.30(s, 3H)<br>5.75(s, 2H)<br>6.4–7.3(m)<br>7.9–8.3(m) |
| 10 | $X_1$ = H<br>$X_2$ = Cl<br>$X_3$ = Cl<br>$X_4$ = H<br>$X_5$ = H | $R_1$ = H<br>$R_2$ = H | 3350, 1775<br>1670 | 5.76(s, 2H)<br>6.9–8.1(m) |
| 11 | $X_1$ = CH$_3$<br>$X_2$ = H<br>$X_3$ = H<br>$X_4$ = Cl<br>$X_5$ = H | $R_1$ = H<br>$R_2$ = H | 3420, 1770<br>1670 | 2.30(s, 3H)<br>5.75(s, 2H)<br>6.8–7.3(m)<br>8.2–8.5(m) |
| 12 | $X_1$ = H<br>$X_2$ = Cl<br>$X_3$ = H<br>$X_4$ = Cl<br>$X_5$ = H | $R_1$ = H<br>$R_2$ = H | 3350, 1770<br>1665 | 5.74(s, 2H)<br>6.8–7.7(m) |
| 13 | $X_1$ = OC$_2$H$_5$<br>$X_2$ = H<br>$X_3$ = H<br>$X_4$ = Cl<br>$X_5$ = H | $R_1$ = H<br>$R_2$ = H | 3400, 1785<br>1765, 1675 | 1.46(t, 3H)<br>4.07(q, 2H)<br>5.72(s, 2H)<br>6.4–7.3,<br>8.2–8.5(m)<br>7.75(m) |
| 14 | $X_1$ = Cl<br>$X_2$ = H<br>$X_3$ = H<br>$X_4$ = Cl<br>$X_5$ = H | $R_1$ = H<br>$R_2$ = H | 3380, 1770<br>1665 | 5.77(s, 2H)<br>6.7–7.4(m)<br>7.65(m)<br>8.3–8.7(m) |
| 15 | $X_1$ = CF$_3$<br>$X_2$ = H<br>$X_3$ = H<br>$X_4$ = H<br>$X_5$ = H | $R_1$ = H<br>$R_2$ = H | 3440, 1790<br>1665 | 5.21(s, 2H)<br>6.4–7.3(m)<br>7.8–8.2(m) |
| 16 | $X_1$ = H<br>$X_2$ = Cl<br>$X_3$ = F<br>$X_4$ = H<br>$X_5$ = H | $R_1$ = H<br>$R_2$ = H | 3380, 1780<br>1665 | 5.74(s, 2H)<br>6.8–8.0(m) |
| 17 | $X_1$ = OC$_2$H$_5$<br>$X_2$ = H<br>$X_3$ = H<br>$X_4$ = OC$_2$H$_5$<br>$X_5$ = H | $R_1$ = H<br>$R_2$ = H | 3410, 1785<br>1670 | 1.39(t, 3H)<br>1.42(t, 3H)<br>3.2–4.3(m)<br>5.72(s, 2H)<br>6.2–8.2(m) |
| 18 | $X_1$ = Cl<br>$X_2$ = H<br>$X_3$ = Cl<br>$X_4$ = Cl<br>$X_5$ = H | $R_1$ = H<br>$R_2$ = H | 3400, 1790<br>1670 | 5.76(s, 2H)<br>7.0–7.8(m)<br>8.5–8.8(s) |
| 19 | $X_1$ = F<br>$X_2$ = H<br>$X_3$ = H<br>$X_4$ = H<br>$X_5$ = H | $R_1$ = H<br>$R_2$ = H | 3390, 1770<br>1660 | 5.73(s, 2H)<br>6.7–8.6(m) |
| 20 | $X_1$ = F<br>$X_2$ = H<br>$X_3$ = H<br>$X_4$ = F<br>$X_5$ = H | $R_1$ = H<br>$R_2$ = H | 3400, 1780<br>1665 | 5.77(s, 2H)<br>6.4–8.5(m) |
| 21 | $X_1$ = Cl<br>$X_2$ = H<br>$X_3$ = CH$_3$<br>$X_4$ = H<br>$X_5$ = H | $R_1$ = H<br>$R_2$ = H | 3390, 1785<br>1665 | 2.31(s, 3H)<br>5.74(s, 2H)<br>6.9–8.5(m) |
| 22 | $X_1$ = Cl<br>$X_2$ = H<br>$X_3$ = H<br>$X_4$ = CH$_3$<br>$X_5$ = H | $R_1$ = H<br>$R_2$ = H | 3390, 1775<br>1670 | 2.37(s, 3H)<br>5.67(s, 2H)<br>6.5–8.5(m) |
| 23 | $X_1$ = OCH$_3$<br>$X_2$ = H<br>$X_3$ = H<br>$X_4$ = OCH$_3$<br>$X_5$ = H | $R_1$ = H<br>$R_2$ = H | 3410, 1780<br>1660 | 3.72(s, 3H)<br>3.81(s, 3H)<br>5.72(s, 2H)<br>6.4–8.3(m) |
| 24 | $X_1$ = H<br>$X_2$ = CF$_3$<br>$X_3$ = H<br>$X_4$ = H | $R_1$ = H<br>$R_2$ = H | 3360, 1775<br>1665 | 5.76(s, 2H)<br>7.0–8.2(m) |

TABLE 1-continued

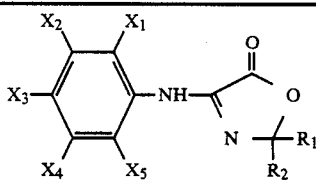

| No. | $X_1, X_2, X_3$ $X_4$ and $X_5$ | $R_1$ and $R_2$ | IR (mp °C.) | N.M.R. (CDCl$_3$) |
|---|---|---|---|---|
| 25 | $X_1 = H$<br>$X_2 = F$<br>$X_3 = CH_3$<br>$X_4 = H$<br>$X_5 = H$ | $R_1 = H$<br>$R_2 = H$ | 3330, 1770<br>1670 | 2.20(s)<br>2.22(s)<br>5.72(s, 2H)<br>6.9–7.8(m) |
| 26 | $X_1 = Cl$<br>$X_2 = H$<br>$X_3 = Cl$<br>$X_4 = H$<br>$X_5 = H$ | $R_1 = H$<br>$R_2 = H$ | 3350, 1780<br>1650 | 5.71(s, 2H)<br>6.9–8.6(m) |
| 27 | $X_1 = H$<br>$X_2 = Cl$<br>$X_3 = CH_3$<br>$X_4 = H$<br>$X_5 = H$ | $R_1 = H$<br>$R_2 = H$ | 3340, 1780<br>1655 | 2.32(s, 3H)<br>5.71(s, 2H)<br>6.8–8.0(m) |
| 28 | $X_1 = H$<br>$X_2 = F$<br>$X_3 = F$<br>$X_4 = H$<br>$X_5 = H$ | $R_1 = H$<br>$R_2 = H$ | 3340, 1780<br>1670 | 5.72(s, 2H)<br>6.6–8.1(m) |
| 29 | $X_1 = H$<br>$X_2 = SCH_3$<br>$X_3 = H$<br>$X_4 = H$<br>$X_5 = H$ | $R_1 = H$<br>$R_2 = H$ | 3360, 1770<br>1665 | 2.47(s, 3H)<br>5.72(s, 2H)<br>6.6–7.7(m) |
| 30 | $X_1 = H$<br>$X_2 = H$<br>$X_3 = COOC_2H_5$<br>$X_4 = H$<br>$X_5 = H$ | $R_1 = H$<br>$R_2 = H$ | 3340, 1770<br>1710, 1670 | 1.37(t, 3H)<br>4.29(q, 2H)<br>5.75(s, 2H)<br>7.0–8.2(m) |
| 31 | $X_1 = NO_2$<br>$X_2 = H$<br>$X_3 = H$<br>$X_4 = H$<br>$X_5 = H$ | $R_1 = H$<br>$R_2 = H$ | 3380, 3300<br>1790, 1660 | |
| 32 | $X_1 = CH_3$<br>$X_2 = F$<br>$X_3 = H$<br>$X_4 = H$<br>$X_5 = H$ | $R_1 = H$<br>$R_2 = H$ | 3440, 1785<br>1670 | |
| 33 | $X_1 = CH_3$<br>$X_2 = F$<br>$X_3 = H$<br>$X_4 = H$<br>$X_5 = H$ | $R_1 = CH_3$<br>$R_2 = CH_3$ | 3370, 1765<br>1660 | |
| 34 | $X_1 = CF_3$<br>$X_2 = H$<br>$X_3 = Cl$<br>$X_4 = H$<br>$X_5 = H$ | $R_1 = H$<br>$R_2 = H$ | 3430, 1780<br>1665 | 5.72(s, 2H)<br>7.0–8.8(m) |
| 35 | $X_1 = CH_3$<br>$X_2 = F$<br>$X_3 = Br$<br>$X_4 = H$<br>$X_5 = H$ | $R_1 = H$<br>$R_2 = H$ | (mp 191° C.) | |
| 36 | $X_1 = CH_3$<br>$X_2 = H$<br>$X_3 = OCHF_2$<br>$X_4 = H$<br>$X_5 = H$ | $R_1 = H$<br>$R_2 = H$ | 3430, 1790<br>1665<br>(mp 103° C.) | 2.32(s, 3H)<br>5.21(s, 2H)<br>6.37(t, 1H)<br>6.7–7.3<br>(m, 3H)<br>8.14(d, 1H) |
| 37 | $X_1 = CH_3$<br>$X_2 = COC_6H_5$<br>$X_3 = H$<br>$X_4 = H$<br>$X_5 = H$ | $R_1 = H$<br>$R_2 = H$ | 3370, 1780<br>1660<br>(mp 150° C.) | 2.22(s, 3H)<br>5.74(s, 2H)<br>6.9–7.8<br>(m, 8H)<br>8.34(d, 1H) |
| 38 | $X_1 = CH_3$<br>$X_2 = F$<br>$X_3 = H$ | $R_1 = CH_3$<br>$R_2 = H$ | | |
| 39 | $X_4 = H$<br>$X_5 = H$<br>$X_1 = CH_3$<br>$X_2 = H$<br>$X_3 = H$<br>$X_4 = F$<br>$X_5 = H$ | $R_1 = C_6H_5$<br>$R_2 = H$ | (mp 118° C.) | |
| 40 | $X_1 = CH_3$<br>$X_2 = F$<br>$X_3 = H$<br>$X_4 = H$<br>$X_5 = H$ | $R_1 = CH_3$<br>$R_2 = C_2H_5$ | 3380, 1775<br>1660 | (δ in CCl$_4$)<br>0.89(t, 3H),<br>1.59(s, 3H),<br>1.92(q, 2H),<br>2.26(d, 3H),<br>6.5–7.3<br>(m, 3H),<br>8.22(1H) |

The herbicides of the present invention which contain as active ingredients the compounds of the general formula [I] exhibit strong herbicidal activities on a wide variety of weeds. When the herbicides of the invention as mentioned above are applied in an amount of 0.1 to 10 kg per 1 hectare in terms of their active ingredient to weeds immediately before germination thereof or at an initial or middle stage of growth thereof, such a great variety of weeds as will be mentioned later can be exterminated or controlled in the course of about 1–2 weeks after application of said herbicides.

When the amount of the herbicides containing the novel compounds of the invention to be applied to is regulated or an appropriate method of application thereof is adopted, weeds can be selectively controlled in the fields where specific firm products are cultivated such as corn, potato, sugar cane, peanut, soybean, sunflower, barley, wheat, sol gum, paddy rice, cotton and fruit tree. When the present herbicides are applied, in particular, to paddy fields, such strong weeds as barnyardgrass, bulrush, water chestnut and water nutsedge can be controlled, and said herbicides exhibit their herbicidal effects on barnyardgrass even when they are applied to barnyardgrass of the 3-leaf stage.

The herbicides of the present invention may be obtained by formulating the above-mentioned compounds of the general formula [I], together with solid or liquid carriers, according to the conventional method of the formulation of agricultural chemicals, into various types of formulations, for example, emulsions, wettable powders, dusts, granules, flowables, etc. In that case, there may be mixed therewith, if necessary, various additives, such as emulsifiers and spreaders, for the purposes intended, and various kinds of surfactants for other purposes and, in addition thereto, other herbicides or agricultural chemicals, for example, insecticides, germicides, nematicides, plant growth regulators, fertilizers, etc., for the purpose of expanding an effective range of the present herbicides.

The herbicides of the invention may be used for controlling a wide variety of weeds, for example, those as exemplified below. That is, such weeds include broadleaved weeds, for example, *Stellaria media, Chenopo-*

*dium album, Sagina japonica, Chenopodium ficifolium, Polygonum nodosum, Portulaca oleracea, Capsella bursapastoris, Lepidium virginicum, Rorippa indica, Cardamine flexuosa, Abutilon theophrasti, Sida spinosa, Ipomoea purpurea, Senecio vulgaris, Sonchus asper, Bidens frondosa, Ambrosia artemisiaefolia, Aster subulatus, Lamium amplexicaule, Oxalis corniculate, Amaranthus retroflexus, Vicia sativa, Galium aparine, Solanum nigrum, Datura stramonium* and the like; grasses of Gramineae, for example, *Poa annua, Alopecurus aequalis, Digitaria adscendens, Eleusine indica, Setaria viridis, Echinochloa crus-galli, Agropyron Kamoji, Lolium perenne, Bromus unioloides, Avena fatua, Polypogon Higegaweri, Panicum dichotomiflorum* and the like; and weeds of Cyperaceae, for example, *Cyperus microiria, Cyperus Iria, Cyperus serotinus, Eleocharis kuroguwai, Eleocharis acicularis* and the like.

The present invention is illustrated below with reference to examples, but it should be construed that the invention is in no way limited to those examples.

PREPARATION EXAMPLE 1

(Compound No. 32)

To a solution of 3-fluoro-2-methylaniline (200 mmol, 25 g) in methylene chloride (70 ml) was added a solution of ethyl imino(ethylthio)acetate hydrogentetrafluorobarate (200 mmol) prepared by a method disclosed in Japanese Patent Laid-open Publication No. 56-39092 in methylene chloride (100 ml), and the mixture was thoroughly shaken and allowed to stand at room temperature for 12 hours. At the end of the period, n-hexane (300 ml) was added to the reaction mixture and the mixture was allowed to stand for 2 hours. After removal of a supernatant by decantation, methylene chloride (200 ml) was added to the remaining mixture, which was then neutralized by addition of an aqueous solution of sodium bicarbonate with thorough stirring. From the resulting mixture an organic phase (a solution in methylene chloride) was separated and dried over anhydrous magnesium sulfate overnight. After removal of inorganic materials by filtration, the filtrate was concentrated under reduced pressure to obtain ethyl imino[(3-fluoro-2-methylphenyl)amino]acetate. The product was dissolved in ethanol (80 ml), and to the resulting solution 37% formalin (30 ml) was added and the mixture was thoroughly shaken and allowed to stand overnight. The crystalline product so produced was filtered and recrystallized from ethanol. A white crystalline product (86 mmol, 18 g) was obtained in a yield of 43%.

PREPARATION EXAMPLE 2

(Compound No. 33)

Ethyl imino [(3-fluoro-2-methylphenyl)amino]acetate was prepared in the manner as described in Preparation Example 1. To this compound (200 mmol), dried acetone (600 ml) and glacial acetic acid (40 ml) were added, and the resulting mixture was refluxed for 24 hours. Upon removal of the solvent under reduced pressure there was produced a crystalline product, which was recrystallized from ethanol. A white crystalline product (34 mmol, 8.0 g) was obtained in a yield of 17%.

PREPARATION EXAMPLE 3

(Compound No. 9)

5-Fluoro-2-methylaniline (40 mmol, 5.0 g) was dissolved in methylene chloride (15 ml). To the solution was added a solution of ethyl imino(ethylthio)acetate hydrogentetrafluoroborate (40 mmol) in methylene chloride (20 ml), and the mixture was thoroughly shaken and allowed to stand at ambient temperature for 12 hours. At the end of the period, n-hexane (60 ml) was added to the reaction mixture and the mixture was allowed to stand for 2 hours. After removal of a supernatant by decantation, methylene chloride (40 ml) was added to the reaction mixture, which was then neutralized by addition of an aqueous solution of sodium bicarbonate with stirring. From the resulting mixture an organic phase (a solution in methylene chloride) was separated and dried over anhydrous magnesium sulfate overnight. After removal of inorganic materials by filtration, the filtrate was concentrated under reduced pressure to provide a syrup of ethyl imino[(5-fluoro-2-methylphenyl)-amino]acetate. The syrup was dissolved in ethanol (20 ml) and to the resulting ethanol solution of 35% formalin (6.0 ml) was added and the mixture was thoroughly shaken and allowed to stand overnight. The crystalline product so produced was filtered and recrystallized from ethanol. A purified crystalline product (10 mmol, 2.1 g) was obtained in a yield of 25 %.

PREPARATION EXAMPLE 4

(Compound No. 39)

Ethyl imino[(5-fluoro-2-methylphenyl)amino]acetate was prepared in the manner as described in Preparation Example 3. This compound (13 mmol) was dissolved in methanol (20 ml). To the solution benzaldehyde (14 mmol, 1.5 g) was added and the mixture was allowed to stand overnight. Upon removal of the solvent under reduced pressure there was produced a crystalline product, which was recrystallized from methanol. A white crystalline product (3.2 mmol, 0.90 g) was obtained in a yield of 25%.

PREPARATION EXAMPLE 5

(Compound No. 40)

Ethyl imino[(3-fluoro-2-methylphenyl)amino]acetate was prepared in the manner as described in Preparation Example 1. To this compound (7.0 mmol) dried ethyl methyl ketone (30 ml) and glacial acetic acid (2.0 ml) were added, and the resulting mixture was refluxed for 10 hours. Upon removal of the solvent under reduced pressure there was produced a crystalline product, which was recrystallized from n-hexane. A white crystalline product (2.0 mmol, 0.50 g) was obtained in a yield of 29%.

PREPARATION EXAMPLE 6

(Compound No. 6)

To a solution of 3-chloro-2-methylaniline (40 mmol, 5.7 g) in methylene chloride (15 ml) was added a solution of ethyl imino(ethylthio)acetate hydrogentetrafluoroborate (40 mmol) in methylene chloride (20 ml), and the mixture was thoroughly shaken and allowed to stand at ambient temperature for 12 hours. At the end of the period, n-hexane (60 ml) was added to the reaction mixture and the mixture was allowed to stand for 2 hours. After removal of a supernatant by decantation, methylene chloride (40 ml) was added to the remaining mixture, which was then neutralized by addition of an aqueous solution of sodium bicarbonate with stirring. From the resulting mixture an organic phase (a solution in methylene chloride) was separated and dried over anhydrous magnesium sulfate overnight. After removal of inorganic materials by filtration, the filtrate was concentrated under reduced pressure to provide ethyl imino[(3-chloro-2-methylphenyl)amino]acetate. The product was dissolved in ethanol (20 ml). To the ethanol solution of 35% formalin (6.0 ml) was added and the mixture was thoroughly shaken and allowed to stand overnight. The crystalline product so produced was filtered and recrystallized from ethanol. A white crystalline product (1.3 mmol, 2.9 g) was obtained in a yield of 33%.

PREPARATION EXAMPLE 7

(Compound No. 36)

Preparation Example 6 was repeated except that 4-difluoromethoxy-2-methylaniline (40 mmol, 6.9 g) was used instead of the 3-chloro-2-methylaniline (40 mmol, 5.7 g) and that the final product was recrystallized from methanol. A white crystalline product (2.3 g) was obtained in a yield of 52%.

Typical formulations of the herbicidal composition according to the invention will now be illustrated by the following Examples, in which parts are by weight.

EXAMPLE 1

(Wettable)

A wettable powder containing 50% by weight of an active ingredient was prepared by mixing and pulverizing a mixture of 50 parts of a compound shown in Table 1 as the active ingredient, 35 parts of talc, 5 parts of diatomaceous earth, 5 parts of white carbon and 5 parts of polyoxyethylene alkylaryl ether.

EXAMPLE 2

(Granule)

A granule containing 10% by weight of an active ingredient was prepared by adding 20 parts of water to a mixture comprising 10 parts of a compound shown in Table 1 as the active ingredient, 30 parts of bentonite, 58 parts of talc and 2 parts of polyoxyethylene alkylaryl ether, kneading the resulting mixture by means of a kneader, granulating the kneadate, and drying the resulting granules followed by screening.

In order to demonstrate herbicidal effects of the compounds according to the invention, some of typical test examples are given below. In the test examples, herbicidal effects and phytotoxicities of the compounds used were visually observed, and the results were shown by a 11-point grading wherein 0 signifies no herbicidal effect or no phytotoxicity and 10 signifies complete withering.

TEST EXAMPLE 1

Flooded soil treatment (before germination of weeds)

A pot having an area of 80 cm$^2$ was filled with a paddy soil and sowed at s surface layer of about 2 cm with seeds of barnyard grass (*Echinochloa crus-galli*), ammania (*Ammania multiflora*) and bulrush (*Soirpus juncoides*), a tuber of water nutsedge (*Cyperus serotinus*) and a paddy rice plant of the bifoliate stage were transplanted in two places, respectively, of the pot, wherein water was maintained at the depth of 3 cm. One day after, a wettable powder prepared in accordance with the procedure of Example 1 and containing each compound indicated in Table 2 was applied into the water. Three weeks after the application of the herbicide, herbicidal effects on the weeds and phytotoxicity to the paddy rice plant were visually observed. The results are shown in Table 2.

TEST EXAMPLE 2

Flooded soil treatment (after germination of weeds)

Test Example 1 was repeated except that the weeds and paddy rice plant were allowed to grow in a green house for 10 days before the application of the herbicide. The results are shown in Table 3.

TABLE 2

| Compound No. | Amount of herbicide applied a.i. kg/ha | Herbicidal effect | | | | Phytotoxicity to rice plant |
|---|---|---|---|---|---|---|
| | | Barnyard-grass | Ammania | Bulrush | Water nutsedge | |
| 1 | 4 | 10 | 10 | 10 | 10 | 0 |
| | 2 | 10 | | 10 | 10 | 0 |
| | 1 | 10 | | 4 | 6 | 0 |
| 2 | 4 | 10 | 10 | 7 | 9 | 0 |
| | 2 | 10 | | 7 | 9 | 0 |
| | 1 | 10 | | 6 | 9 | 0 |
| 4 | 4 | 10 | 10 | 10 | 10 | 0 |
| | 2 | 10 | | 8 | 9 | 0 |
| 5 | 4 | 10 | 8 | 7 | 5 | 0 |
| 6 | 4 | 10 | 10 | 10 | 10 | 2 |
| | 2 | 10 | | 10 | 10 | 0 |
| 7 | 4 | 10 | 9 | 9 | 8 | 0 |
| | 2 | 9 | | 5 | 5 | 0 |
| 8 | 4 | 10 | 10 | 10 | 9 | 0 |
| | 2 | 8 | | 5 | 6 | 0 |
| 9 | 4 | 10 | 10 | 9 | 10 | 2 |
| | 2 | 10 | | 4 | 10 | 0 |
| 10 | 4 | 10 | 10 | 6 | 10 | 0 |
| | 2 | 9 | | 2 | 7 | 0 |
| 16 | 4 | 10 | 10 | 9 | 10 | 0 |
| | 2 | 10 | | 9 | 10 | 0 |
| 17 | 4 | 10 | | 7 | 10 | 0 |
| 19 | 4 | 8 | | 6 | 8 | 0 |
| 25 | 4 | 8 | | 5 | 7 | 0 |
| | 2 | 8 | | 2 | 0 | 0 |
| 27 | 4 | 8 | | 4 | 8 | 0 |
| | 2 | 6 | | 2 | 6 | 0 |
| 28 | 4 | 10 | 10 | 9 | 10 | 2 |
| | 2 | 10 | | 8 | 8 | 0 |

TABLE 2-continued

| Compound No. | Amount of herbicide applied a.i. kg/ha | Herbicidal effect | | | | Phytotoxicity to rice plant |
|---|---|---|---|---|---|---|
| | | Barnyardgrass | Ammania | Bulrush | Water nutsedge | |
| 32 | 4 | 10 | 10 | 10 | 10 | 2 |
|  | 2 | 10 |  | 8 | 10 | 0 |
|  | 1 | 10 |  | 5 | 9 | 0 |
| 33 | 4 | 10 | 8 | 8 | 10 | 2 |
|  | 2 | 10 |  | 7 | 10 | 0 |
|  | 1 | 10 |  | 7 | 10 | 0 |
| 35 | 4 | 7 | 5 | 7 | 0 | 0 |
| 36 | 4 | 10 |  | 0 | 0 | 0 |
| 37 | 4 | 10 |  | 2 | 6 | 0 |
| 38 | 4 | 10 | 10 | 10 | 10 | 2 |
|  | 2 | 10 |  | 0 | 9 | 0 |
| 39 | 4 | 7 | 7 | 10 | 10 | 0 |
| 40 | 4 | 10 | 10 | 9 | 10 | 2 |
|  | 2 | 10 | 10 | 8 | 10 | 0 |
|  | 1 | 10 | 10 | 5 | 9 | 0 |
| Control* | 4 | 10 | 10 | 10 | 8 | 5 |

*Prechilachlor

TABLE 3

| Compound No. | Amount of herbicide applied a.i. kg/ha | Herbicidal effect | | | | Phytotoxicity to rice plant |
|---|---|---|---|---|---|---|
| | | Barnyardgrass | Ammania | Bulrush | Water nutsedge | |
| 2 | 4 | 10 | 10 | 10 | 10 | 0 |
|  | 2 | 6 |  | 8 | 8 | 0 |
| 4 | 4 | 10 | 10 | 10 | 10 | 0 |
|  | 2 | 10 |  | 9 | 10 | 0 |
|  | 1 | 7 |  | 6 | 8 | 0 |
| 6 | 4 | 10 |  | 10 | 10 | 0 |
|  | 2 | 8 |  | 9 | 9 | 0 |
| 16 | 4 | 10 |  | 6 | 4 | 0 |
|  | 2 | 10 |  | 4 | 0 | 0 |
| 19 | 4 | 8 | 10 | 8 | 2 | 0 |
|  | 2 | 5 |  | 6 | 0 | 0 |
| 28 | 4 | 10 | 10 | 10 | 6 | 0 |
|  | 2 | 10 |  | 10 | 5 | 0 |
| 32 | 4 | 10 | 10 | 10 | 10 | 2 |
|  | 2 | 10 |  | 10 | 10 | 0 |
|  | 1 | 10 |  | 9 | 10 | 0 |
| 33 | 4 | 10 | 10 | 10 | 10 | 2 |
|  | 2 | 10 |  | 8 | 8 | 0 |
| Control* | 4 | 9 | 7 | 9 | 5 | 3 |

*Prechilachor

What is claimed is:

1. A compound represented by the formula I:

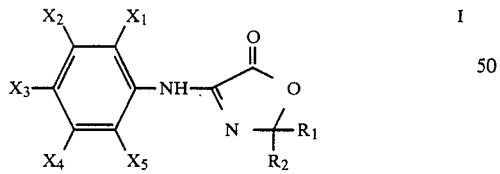

wherein $X_1$, $X_2$, $X_3$, $X_4$ and $X_5$ are each hydrogen, halogen, a lower alkyl, a lower alkoxy, a lower alkylthio, trifluoromethyl, difluoromethoxy, a lower alkoxycarbonyl, nitro, an alkanoyl or an aroyl, provided that $X_1$-$X_5$ are neither all nitro nor all tert-butyl, and that not more than two of $X_1$-$X_5$ are iodo, and $R_1$ and $R_2$ are each hydrogen, a lower alkyl or phenyl, or a lower alkyl or phenyl substituted with at least one halogen atom, provided further that a lower alkyl or phenyl which is substituted with at least one halogen atom, is not substituted with more than two iodine atoms.

2. The compound as claimed in claim 1 wherein $X_1$ is methyl, $X_2$ is fluorine or chlorine, $X_3$, $X_4$ and $X_5$ are each hydrogen and $R_1$ and $R_2$ are each hydrogen or methyl.

3. The compound as claimed in claim 2 wherein $X_1$ is methyl, $X_2$ is fluorine, $X_3$, $X_4$ and $X_5$ are each hydrogen and $R_1$ and $R_2$ are each hydrogen or methyl.

4. The compound as claimed in claim 1 wherein $X_1$ is methyl, $X_2$ is fluorine, $X_3$, $X_4$ and $X_5$ are each hydrogen, $R_1$ and $R_2$ are each hydrogen.

5. The compound as claimed in claim 1 wherein $X_1$ is methyl, $X_2$ is chlorine, $X_3$, $X_4$ and $X_5$ are each hydrogen, and $R_1$ and $R_2$ are each hydrogen.

6. The compound as claimed in claim 1 wherein $X_1$ is methyl, $X_2$ is fluorine, $X_3$, $X_4$ and $X_5$ are each hydrogen, and $R_1$ and $R_2$ are each methyl.

7. A herbicide containing as its active ingredient a compound represented by the formula I:

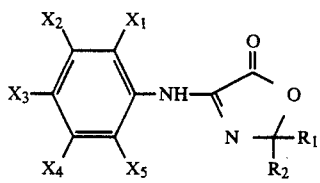

wherein $X_1$, $X_2$, $X_3$, $X_4$ and $X_5$ are each hydrogen, halogen, a lower alkyl, a lower alkoxy, a lower alkylthio, trifluoromethyl, difluoromethoxy, a lower alkoxycarbonyl, nitro, an alkanoyl or an aroyl, provided that $X_1$–$X_5$ are neither all nitro nor all tert-butyl, and that not more than two of $X_1$–$X_5$ are iodo, and $R_1$ and $R_2$ are each hydrogen, a lower alkyl or phenyl, or a lower alkyl or phenyl substituted with at least one halogen atom, provided further that a lower alkyl or phenyl which is substituted with at least one halogen atom is not substituted with more than two iodine atoms.

8. The herbicide as claimed in claim 7 wherein $X_1$ is methyl, $X_2$ is chlorine or fluorine, $X_3$, $X_4$ and $X_5$ are hydrogen and $R_1$ and $R_2$ are each hydrogen or methyl.

9. The herbicide as claimed in claim 7 wherein $X_1$ is methyl, $X_2$ is fluorine, $X_3$, $X_4$ and $X_5$ are each hydrogen and $R_1$ and $R_2$ are each hydrogen or methyl.

* * * * *